United States Patent
Chin et al.

(10) Patent No.: US 8,690,924 B2
(45) Date of Patent: Apr. 8, 2014

(54) SPINAL SCREW ASSEMBLY

(75) Inventors: Kingsley R. Chin, Hallandale, FL (US); Craig Henshaw, Charlestown, MA (US); Matthew Ibarra, Lakewood, CA (US); Todd Saunders, Boston, MA (US)

(73) Assignee: Spinefrontier Inc, Beverly, MA (US)

( * ) Notice: Subject to any disclaimer, the term of this patent is extended or adjusted under 35 U.S.C. 154(b) by 414 days.

(21) Appl. No.: 13/014,765

(22) Filed: Jan. 27, 2011

(65) Prior Publication Data

US 2011/0190821 A1    Aug. 4, 2011

Related U.S. Application Data

(60) Provisional application No. 61/301,346, filed on Feb. 4, 2010.

(51) Int. Cl.
*A61B 17/70* (2006.01)

(52) U.S. Cl.
USPC ......................................................... 606/264

(58) Field of Classification Search
USPC ......... 606/246, 258, 260, 264–272, 278, 279, 606/301, 305, 308; 411/393, 533; 403/187, 403/362, 399
See application file for complete search history.

(56) References Cited

U.S. PATENT DOCUMENTS

| | | | |
|---|---|---|---|
| 4,988,351 A | 1/1991 | Paulos et al. | |
| 5,931,869 A | 8/1999 | Boucher et al. | |
| 7,563,275 B2 | 7/2009 | Falahee et al. | |
| 2002/0007182 A1 | 1/2002 | Kim | |
| 2003/0105465 A1 | 6/2003 | Schmieding et al. | |
| 2004/0143268 A1 | 7/2004 | Falahee | |
| 2005/0234459 A1 | 10/2005 | Falahee et al. | |
| 2006/0052784 A1 | 3/2006 | Dant et al. | |
| 2006/0217713 A1 | 9/2006 | Serhan et al. | |
| 2006/0217714 A1 | 9/2006 | Serhan et al. | |
| 2006/0217715 A1 | 9/2006 | Serhan et al. | |
| 2006/0264933 A1 | 11/2006 | Baker et al. | |
| 2007/0162023 A1 | 7/2007 | Schock | |
| 2008/0086131 A1 | 4/2008 | Daly et al. | |
| 2008/0255622 A1 | 10/2008 | Mickiewicz et al. | |
| 2009/0192551 A1 | 7/2009 | Cianfrani et al. | |
| 2009/0248089 A1 | 10/2009 | Jacofsky et al. | |
| 2009/0312798 A1 | 12/2009 | Varela | |
| 2009/0312800 A1 | 12/2009 | Chin et al. | |
| 2009/0318968 A1 | 12/2009 | Duggal et al. | |
| 2010/0106195 A1 | 4/2010 | Serhan et al. | |

*Primary Examiner* — Pedro Philogene
*Assistant Examiner* — David Comstock
(74) *Attorney, Agent, or Firm* — AKC Patents LLP; Aliki K. Collins (57) ABSTRACT

A spinal screw assembly includes a bone-anchoring member, a washer, and a seat. The bone-anchoring member includes a main shaft, a washer head, and a spherical head. The spherical head extends upward from the top end of the main shaft and the washer head extends laterally from a location of the main shaft between the main shaft's top end and bottom end. The washer is polyaxially rotatable and positionable around the washer head and is configured to be placed at a first angle relative to the main shaft. The seat is polyaxially rotatable and positionable around the spherical head independent from the washer and is configured to be placed at a second angle relative to the main shaft, wherein the second angle is independent from the first angle.

20 Claims, 13 Drawing Sheets

SPINAL SCREW ASSEMBLY

CROSS REFERENCE TO RELATED CO-PENDING APPLICATIONS

This application claims the benefit of U.S. provisional application Ser. No. 61/301,346 filed Feb. 4, 2010 and entitled "SPINAL SCREW ASSEMBLY", the contents of which are expressly incorporated herein by reference.

FIELD OF THE INVENTION

The present invention relates to a system and a method for facet fixation and spinal stabilization, and more particularly to a spinal screw assembly including a polyaxial screw, and a washer with protrusions to be used with spinal stabilization rods.

BACKGROUND OF THE INVENTION

The human spine consists of individual vertebras that are connected to each other. Under normal circumstances, the structures that make up the spine function to protect the neural structures and to allow us to stand erect, bear axial loads, and be flexible for bending and rotation. However, disorders of the spine occur when one or more of these spine structures are abnormal. In these pathologic circumstances, surgery may be tried to restore the spine to normal, achieve stability, protect the neural structures, or to relieve the patient of discomfort. The goal of spine surgery for a multitude of spinal disorders, especially those causing compression of the neural structures, is often decompression of the neural elements and/or fusion of adjacent vertebral segments. Fusion works well because it stops pain due to movement at the facet joints or intervertebral discs, holds the spine in place after correcting deformity, and prevents instability and or deformity of the spine after surgical procedures such as discectomies, laminectomies, or corpectomies. Discectomy and fusion or corpectomy and fusion are most commonly performed on the cervical spine but there is also increasing application on the thoracic and lumbar spine.

Several spinal fixation systems exist for stabilizing the spine so that bony fusion is achieved. The majority of these fixation systems utilize fixation elements such as rods, wires, or plates that attach to screws threaded into the vertebral bodies, facets, or the pedicles. Because the outer surface of the vertebral body is typically non-planar and the structure of the vertebras is relatively complex, it is important that the fixation elements (e.g., rods, plates, wires, staples and/or screws) are properly aligned when they are inserted into the vertebras. Improper alignment may result in improper or unstable placement of the fixation element and/or disengagement of the fixation element. Achieving and maintaining accurate positioning and guidance of these fixation elements, however have proven to be quite difficult in practice. Such positioning difficulties are further complicated by the fact that the alignment angle for a fixation device through one vertebral body or pair of vertebral bodies will be unique to that individual due to individual differences in the spinal curvature and anatomies. Accordingly, there is a need for a spinal fixation assembly that provides flexibility and polyaxial positioning of the fixation elements, preferably independent from each other.

SUMMARY OF THE INVENTION

The present invention relates to a spinal screw assembly, and in particular to a spinal screw assembly used in connection with spinal stabilization rods.

In general, in one aspect, the invention features a spinal screw assembly including a bone-anchoring member, a washer, and a seat. The bone-anchoring member includes a main shaft, a washer head and a spherical head. The spherical head extends upward from the top end of the main shaft and the washer head extends laterally from a location of the main shaft between the main shaft's top end and bottom end. The washer is polyaxially rotatable and polyaxially positionable around the washer head and is configured to be placed at a first angle relative to the main shaft. The seat is polyaxially rotatable and polyaxially positionable around the spherical head independent from the washer and is configured to be placed at a second angle relative to the main shaft. The second angle is independent from the first angle.

Implementations of this aspect of the invention may include one or more of the following features. The seat comprises a tulip-shaped body having a semispherical inner bottom portion and a cylindrical side portion extending upward from the bottom portion. The bottom portion is configured to hold the spherical head and has a diameter equal or larger than the diameter of the spherical head. The bottom portion further has a through-opening dimensioned to receive and allow the main shaft to pass through and to prevent the spherical head from passing therethrough, while allowing the tulip shaped seat to polyaxially rotate and be polyaxially positioned around the spherical head. The spinal screw assembly further includes a stabilization rod placed perpendicular to the main shaft. The cylindrical side portion of the seat has a horizontal channel dimensioned to receive the stabilization rod. The spinal screw assembly further includes a rod seat and the rod seat has a diameter equal or smaller than the diameter of the cylindrical side portion and is configured to be placed within the cylindrical side portion. The rod seat has a channel configured to hold the stabilization rod. The spinal screw assembly further includes a cap and the cap has a ring-shaped body having outer threads in the outer surface of the ring-shaped body and inner threads in the inner surface of the ring-shaped body. The cap is configured to be placed on top of the stabilization rod and the outer threads are dimensioned to engage inner threads formed in the upper inner portion of the cylindrical side portion of the seat. The spinal screw assembly further includes a rod-locking element comprising outer threads configured to engage the inner threads of the cap and thereby to lock the stabilization rod within the seat. The washer head has a flat top and a semispherical bottom. The washer has a cylindrical top portion and an outward extending bottom portion and protrusions extending downward from the bottom portion. The washer has a semispherical through-opening extending from the top portion to the bottom portion and being dimensioned to receive the washer head and to prevent the washer head from passing therethrough while allowing the washer to polyaxially rotate and be polyaxially positioned around the washer head. The main shaft further has bone engaging outer threads located near its bottom end. The spherical head has a hexagonal top opening and the hexagonal top opening extends into a cylindrical opening of the main shaft and the cylindrical opening extends from the main shaft's top end to its bottom end. The main shaft has an adjustable length. The main shaft has an upper portion and a lower portion and the upper portion includes the spherical head extending from its top end and the lower portion includes the washer head. The upper portion has an adjustable length and thereby the spherical head is positionable at an adjustable distance from the washer head. The upper portion of the main shaft further includes a threaded bottom end and the washer head has a threaded inner opening dimensioned to receive and engage the threaded bottom end of the upper portion. Threading the threaded bottom end of the upper portion in or out of the threaded inner opening of the washer head adjusts the length of the main shaft. The seat has a cylindrical body having outer threads on its outer surface and having a semispherical inner bottom portion. The bottom portion is configured to hold the spherical head and comprises a diameter equal or larger than the diameter of the spherical head. The spinal screw assembly further includes a stabilization rod placed in line with the main shaft and having a spherical end and the spherical end is configured to be placed within the cylindrical body and on top of the spherical head. The spinal screw assembly further includes an outer cylindrical cap having inner threads and the inner threads are dimensioned to engage the outer threads of the seat's cylindrical body. The spinal screw assembly further includes a rod seat dimensioned to be placed within the seat's cylindrical body. The rod seat includes a cylindrical ring having a spherical inner wall dimensioned to receive the spherical head. The stabilization rod includes first and second rod components pivotally connected to each other.

In general, in another aspect, the invention features a method for polyaxially positioning a washer and a seat relative to a main shaft of a spinal screw assembly independent from each other. The method includes providing a bone-anchoring member having a main shaft, a washer head and a spherical head. The spherical head extends upward from the top end of the main shaft and the washer head extends laterally from a location of the main shaft between the main shaft's top end and bottom end. Next, the method includes providing a washer polyaxially rotatable and polyaxially positionable around the washer head and placing the washer at a first angle relative to the main shaft. Next, the method includes providing a seat polyaxially rotatable and polyaxially positionable around the spherical head independent from the washer and placing the seat at a second angle relative to the main shaft. The second angle is independent from the first angle.

The details of one or more embodiments of the invention are set forth in the accompanying drawings and description below. Other features, objects and advantages of the invention will be apparent from the following description of the preferred embodiments, the drawings, and the claims.

BRIEF DESCRIPTION OF THE DRAWINGS

Referring to the figures, wherein like numerals represent like parts throughout the several views.

DETAILED DESCRIPTION OF THE INVENTION

The present invention relates to spinal screw assemblies used in connection with spinal stabilization rods.

Figure 1:
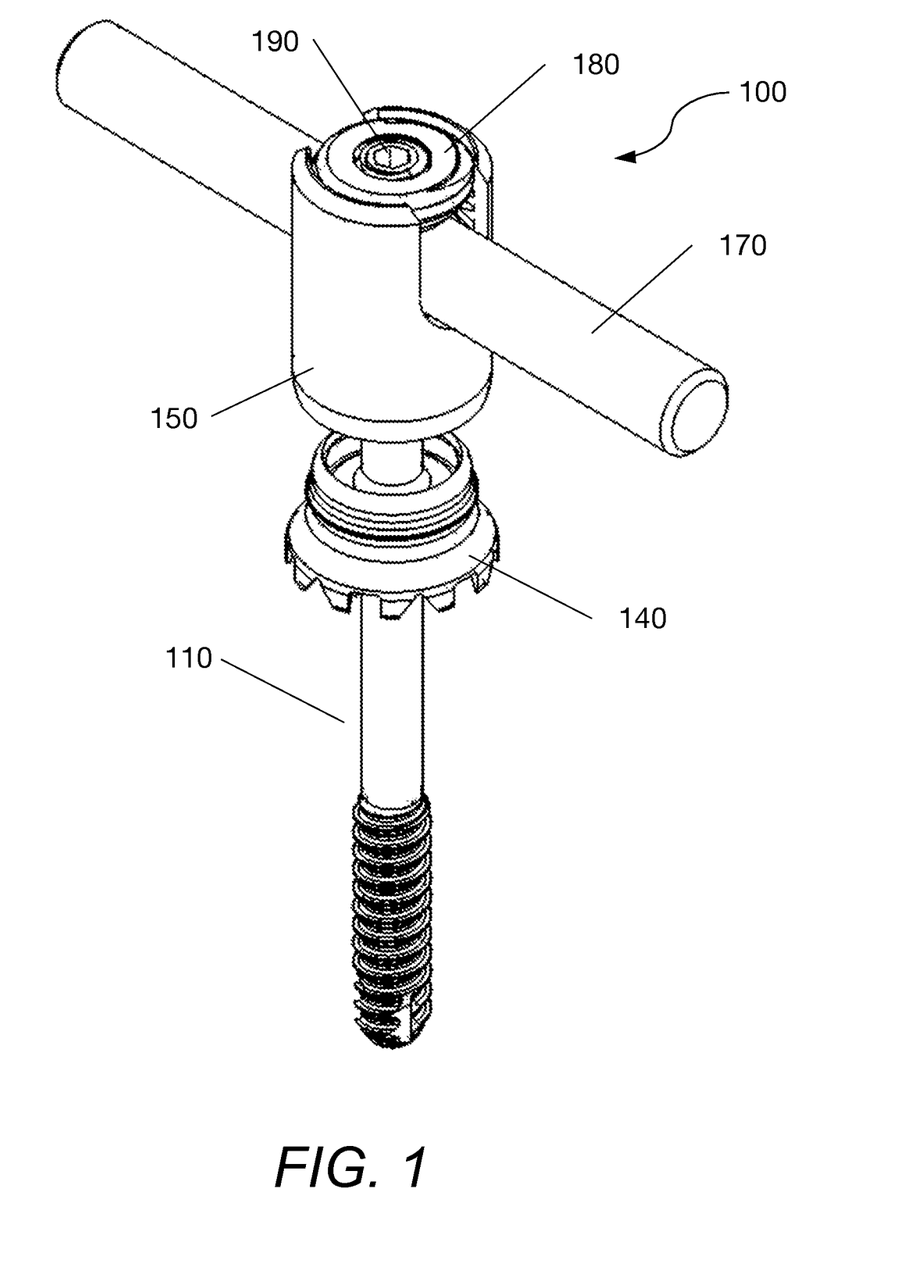
FIG. 1 is a perspective view of a first embodiment of the spine fixation device.
Figure 2A:
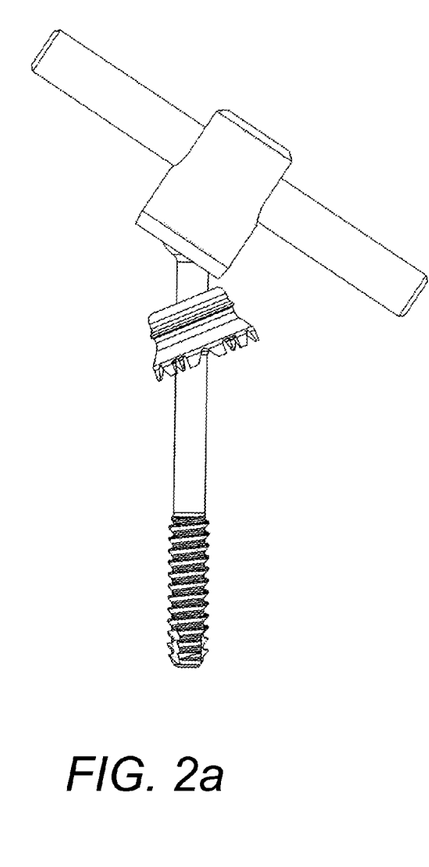
FIG. 2A is a side view of the spine fixation device of FIG. 1 with the tulip-shaped seat and stabilization rod at an angle relative to the bone-anchoring member.
Figure 2B:
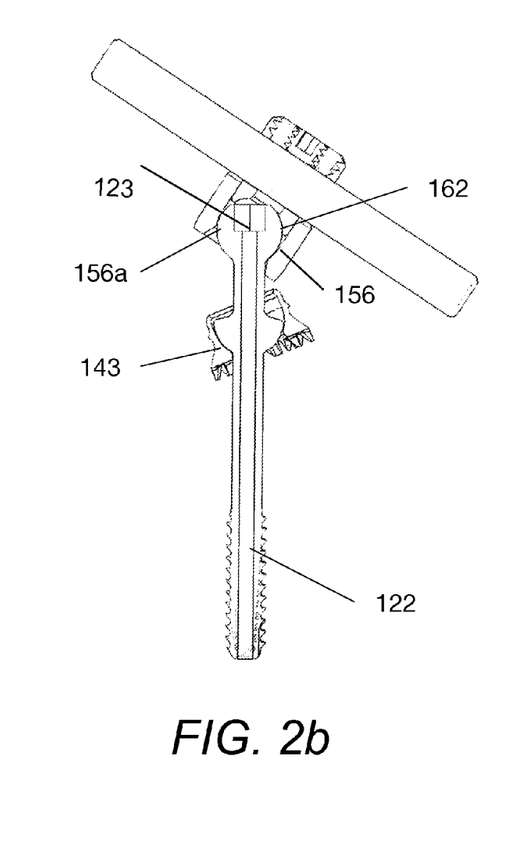
FIG. 2B is a cross-sectional view of the spine fixation device of FIG. 2A.
Figure 3:
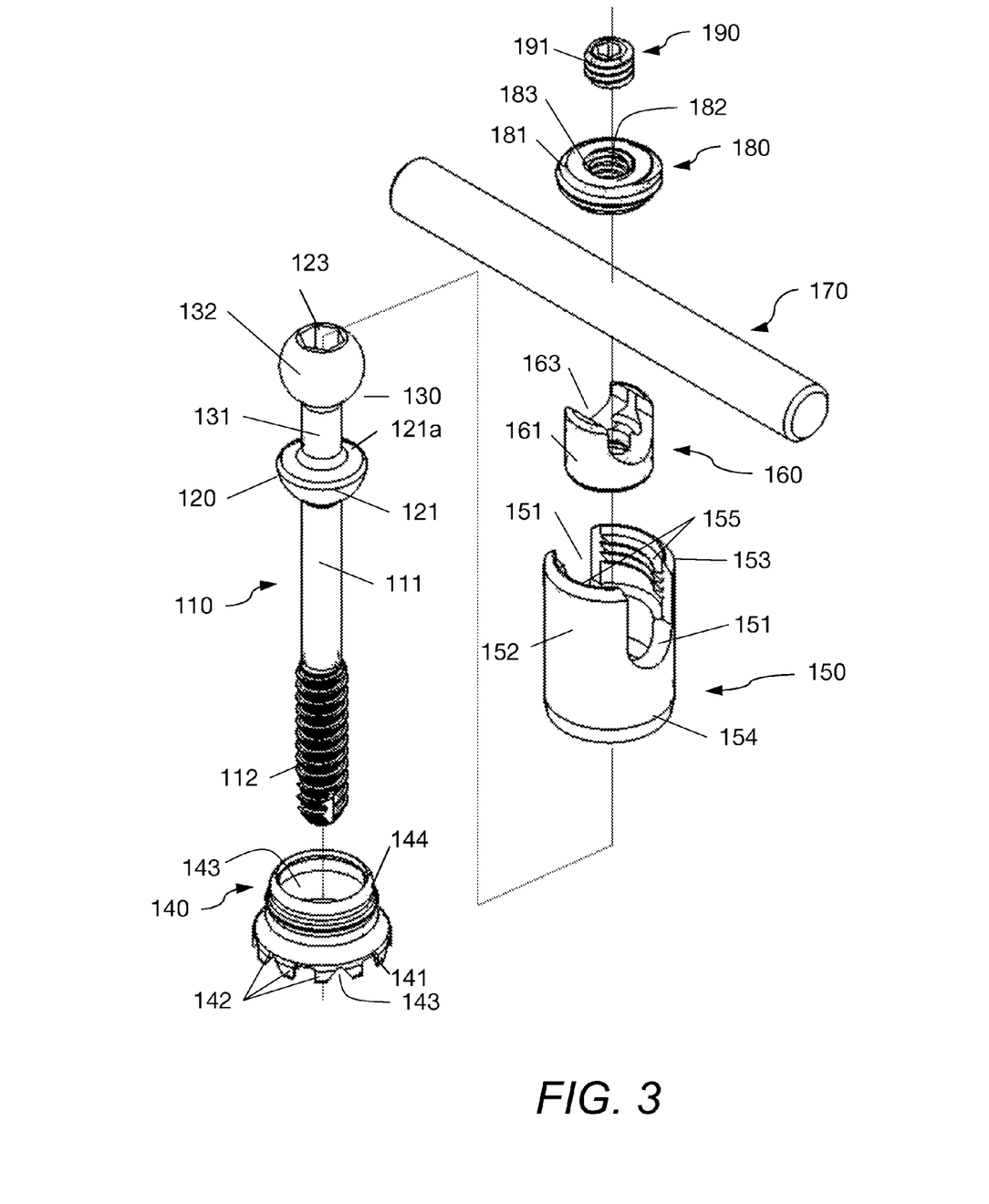
FIG. 3 is an exploded view of the spine fixation device of FIG. 1.
Figure 4:
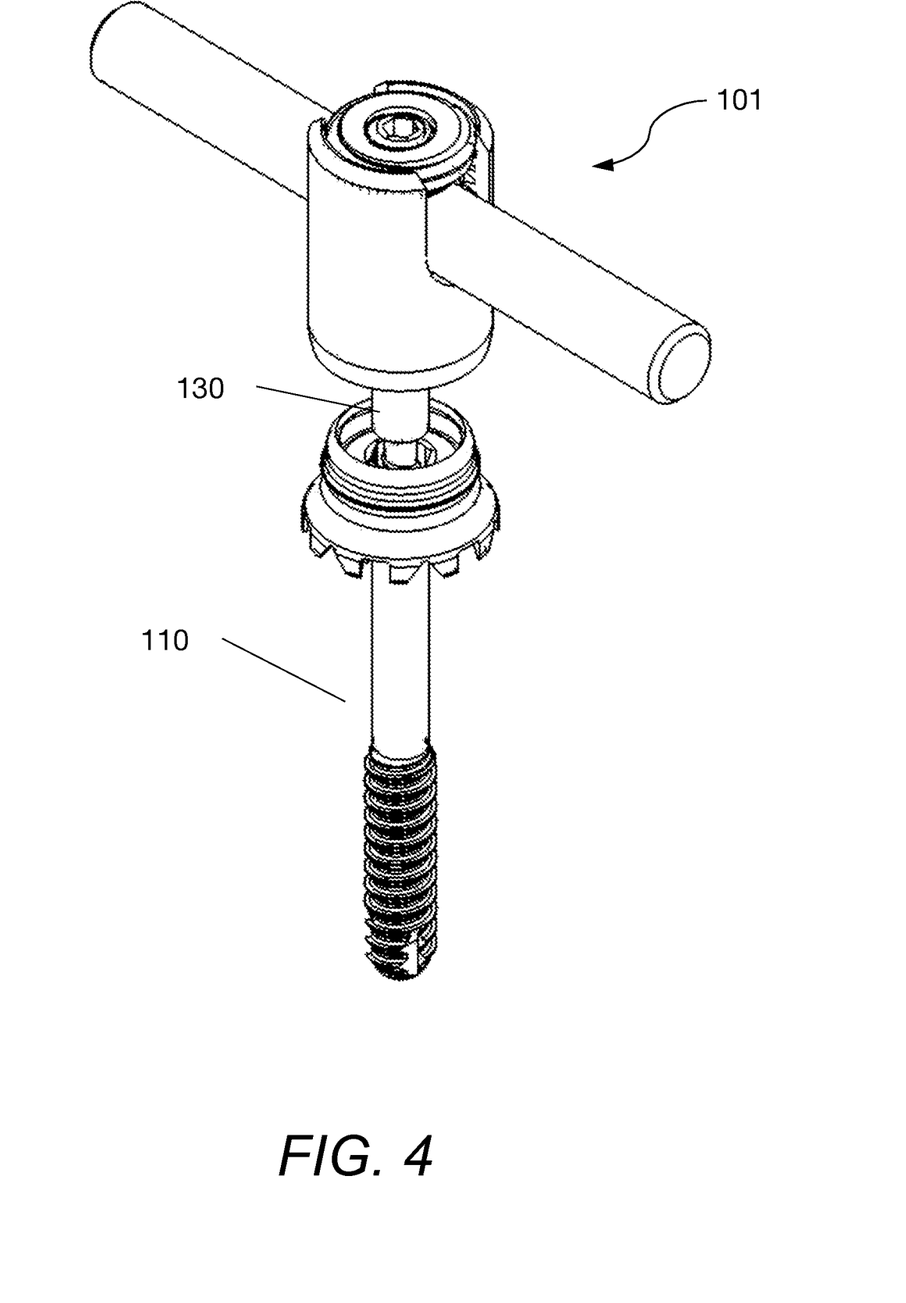
FIG. 4 is a perspective view of a second embodiment of the spine fixation device having a tulip-shaped seat arranged at an adjustable height relative to the bone-anchoring member.

Referring to FIG. 1 to FIG. 3, a spinal screw assembly 100 includes a bone-anchoring member 110, a washer 140, a tulip-shaped seat 150, a stabilization rod 170, a rod seat 160, a cap 180 and a locking element 190.

The bone-anchoring member 110 is usually a screw having outer threads. Referring to FIG. 3, the bone-anchoring member 110 includes a main shaft 111, a washer head 120 and an upper post portion 130. The main shaft 111 includes outer threads 112 at the distal end and the washer head 120 at the proximal end. Washer head 120 has a flat top 121a and a semispherical lower portion 121. Upper post portion 130 includes an upper shaft 131 extending from the flat top 121a of the washer head 120 and terminating to a spherical head 132. Spherical head 132 has a hexagonal top opening 123, which extends into a cylindrical through-opening 122. Cylindrical through-opening 122 extends from about the center of the spherical head 132 through the upper shaft 131, through the main shaft 110 to the distal end of the bone-anchoring member 110. Washer 140 includes a cylindrical top portion 144 and a flat bottom surface 141 having protrusions 142 extending from it. Protrusions 142 are dimensioned to bite and grip onto the facet surface. A semispherical through-opening 143 extends from the top portion 144 to the bottom surface 141 with the spherically shaped portion arranged toward the bottom surface 141. Opening 143 is shaped and dimensioned to receive the washer head 120, as shown in FIG. 2b, and allows the washer head 120 to rotate within the washer 140 and to be oriented together with the bone-anchoring member 110 at an angle relative to the washer 140. The tulip-shaped seat 150 includes a cylindrical base 154 and two side portions 152, 153 extending from the base 154 and forming a U-shaped slot 151 between them, as shown in FIG. 3. The U-shaped slot 151 is shaped and dimensioned to receive the stabilization rod 170. The tulip-shaped seat 150 has a cylindrical through-opening 156 terminating into a semi-spherical bottom 156a. Opening 156 is dimensioned to receive the spherical head 132 in the semi-spherical bottom 156a without letting it go through (as shown in FIG. 2b). The spherical head 132 is allowed to rotate in the semi-spherical bottom 156a and to be oriented at an angle relative to the tulip-shaped seat 150. The tulip-shaped seat 150 has grooves and cuts 155 along the sides 152 and 153. These grooves and cuts 155 may be threaded cuts, straight grooves, or barbed cuts. The rod seat 160 includes a cylinder 161 having a U-shaped side slot 163 and a spherical cut out 162 at the bottom side, as shown in FIG. 2b. The spherical cut out 162 is dimensioned to fit concentrically on top of the spherical head 132. The rod seat 160 is designed and dimensioned to fit inside the tulip-shaped seat 150 and the U-shaped slot 163 is shaped and dimensioned to receive the stabilization rod 170. The cap 180 is comprised of a cylinder with outer threads 181, dimensioned to engage the cuts 155 along the sides 152, 153 of the tulip-shaped seat. Cap 180 also includes a center through hole 182 extending from top to bottom and inner threads 183 running along the inner walls of the through hole 182. The locking element 190 is comprised of a cylinder that is shaped and dimensioned to fit within the center through hole 182 and includes threads 191 on its outer wall. Threads 191 are designed and dimensioned to engage the inner threads 183 of the cap 180 and thereby to compress down and lock in position the stabilization rod 170, rod seat 160, tulip-shaped seat 150, and the bone-anchoring member 110.

In operation, the bone-anchoring member 110 is pre-attached to the washer 140, the tulip-shaped seat 150 and rod seat 160. As was mentioned above, the washer head 120 is allowed to rotate within the washer opening 143 so that the bone-anchoring member 110 is placed at an angle relative to the washer 140. Similarly, the spherical head 132 is allowed to rotate in the semi-spherical bottom 156a of the tulip shaped seat 150 so that the bone-anchoring member 110 is also placed at an angle relative to the tulip-shaped seat 150. The bone-anchoring member 110 is driven through the facet joint along a transpedicular axis, thereby binding the facet joints together and stabilizing them in place. The washer 140 is rotated around the washer head 120 to be arranged at a desired orientation relative to the facet surfaces and then the protrusions 142 bite and grip into the facet surfaces and thereby secure the washer 140 to the facet surfaces. The tulip-shaped seat 150 is then rotated around the spherical head 132 to be arranged at a desired orientation and then it is articulated to receive the stabilization rod 170 for stabilizing another vertebra. Once the stabilization rod 170 is in place and has the desired orientation, the cap 180 is placed in the tulip-shaped seat 150 and its outer threads 181 engage the grooves 155 of the seat 150 to loosely hold the rod 170 in place. Once the assembly is in the desired position and orientation, the locking element 190 is screwed into the central through-opening 182 of the cap 180 to lock down the stabilization rod 170, the rod seat 160, the tulip-shaped seat 150, and the bone-anchoring member 110 and thereby to achieve spinal stabilization.

Figure 7:
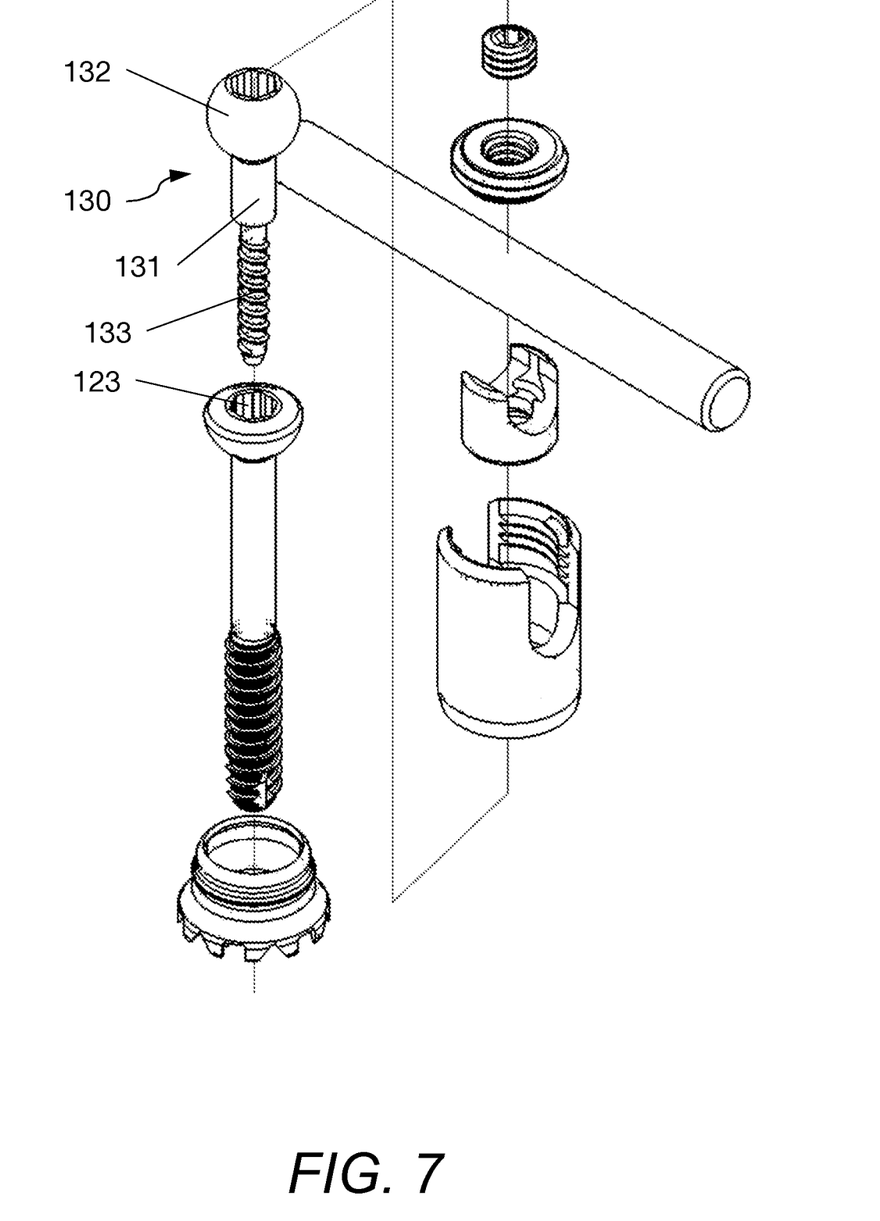
FIG. 7 is an exploded view of the spine fixation device of FIG. 4.

Referring to FIG. 4-FIG. 7, in a second embodiment 101, the upper post portion 130 of the bone-anchoring member 110 is a separate component from the bone-anchoring member 110. In this embodiment, the upper post portion 130 also includes a threaded shaft 133 as shown in FIG. 7. The washer head 120 of the bone-anchoring member 110 includes a hexagonal opening 123 on the flat top 121a. Opening 123 is shaped and dimensioned to receive a hexagonal screwdriver for driving the bone-anchoring member 110 into place. Opening 123 extends into cylindrical opening 122 which now includes inner threads 124 designed and dimensioned to receive and engage the threaded shaft 133 of the upper post portion 130, as shown in FIG. 6a.

Figure 5A:
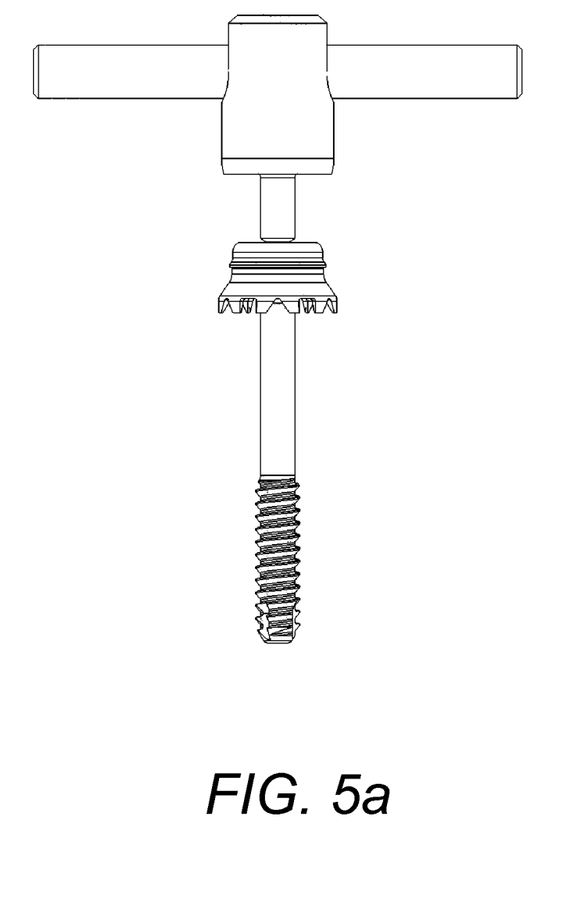
FIG. 5A is a side view of the spine fixation device of FIG. 4 with the tulip-shaped seat arranged at a tall height relative to the bone-anchoring member.
Figure 5B:
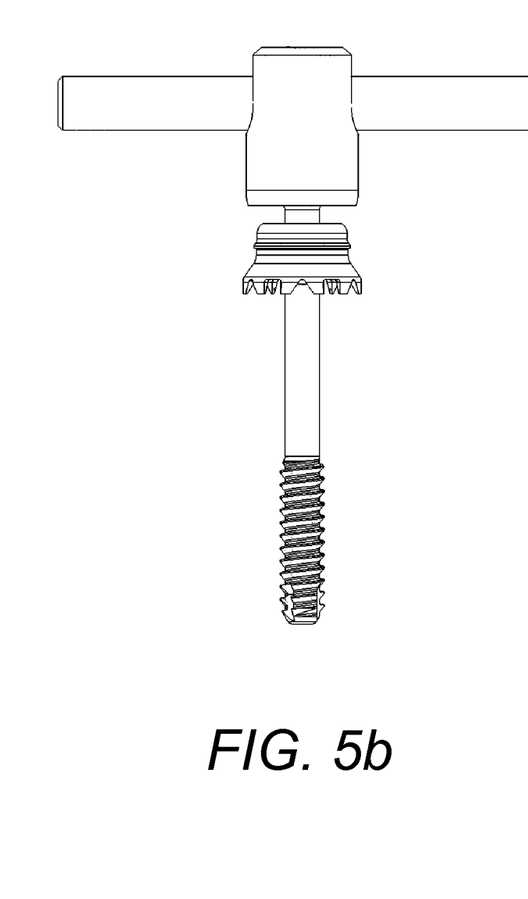
FIG. 5B is a side view of the spine fixation device of FIG. 4 with the tulip-shaped seat arranged at a short height relative to the bone-anchoring member.
Figure 6A:
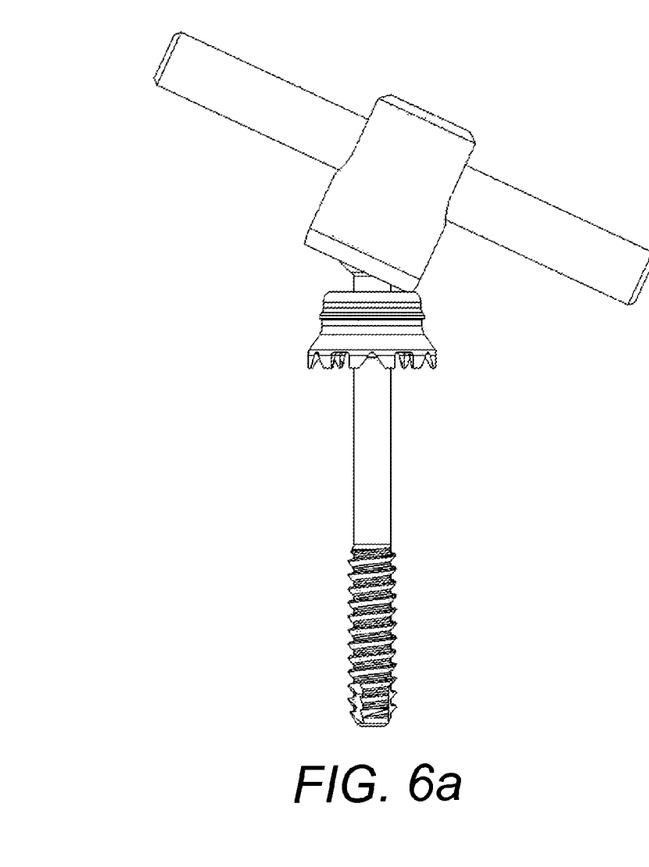
FIG. 6A is a side view of the spine fixation device of FIG. 4 with the tulip-shaped seat and the stabilization rod at an angle relative to the bone-anchoring member.
Figure 6B:
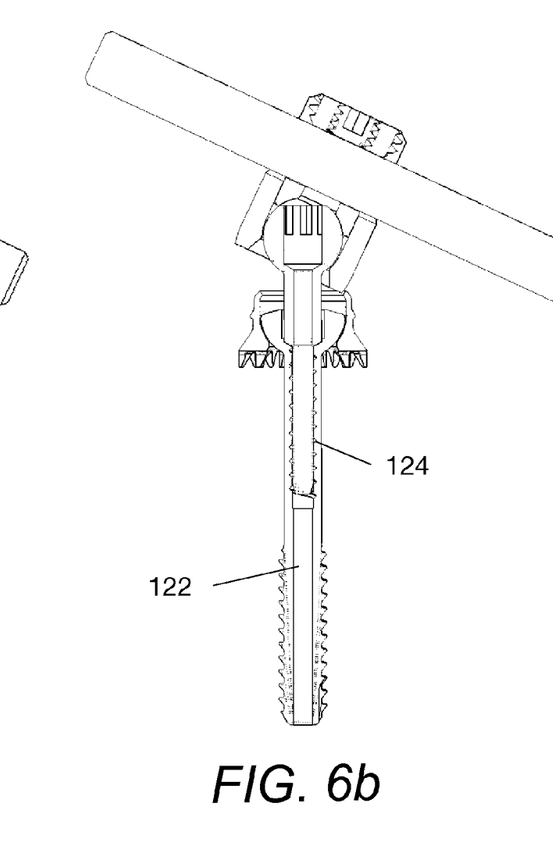
FIG. 6B is a cross-sectional view of the spine fixation device of FIG. 6A.

This embodiment allows for adjustable height positioning of the tulip-shaped seat and thereby of the stabilization rod. The upper post portion 130 is driven in or out to achieve a desired height or distance between the polyaxial washer head 120 and the spherical head 132, as shown in FIGS. 5a and 5b.

Figure 8:
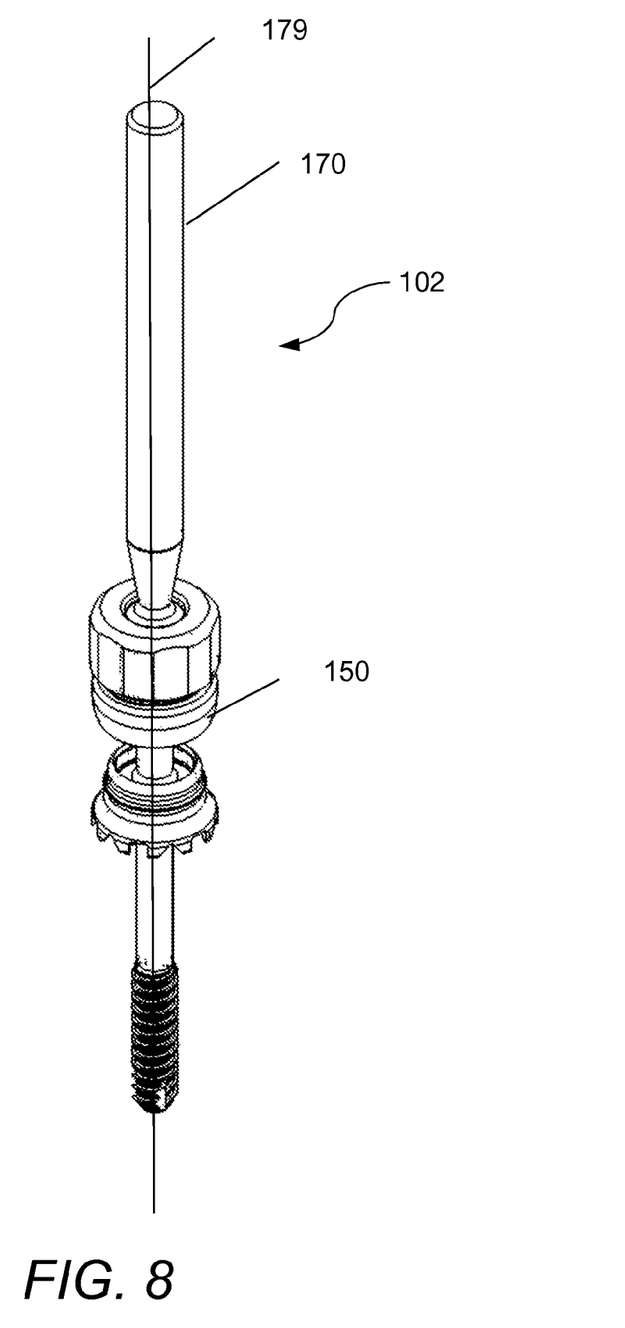
FIG. 8 is a perspective view of a third embodiment of the spine fixation device.
Figure 9A:
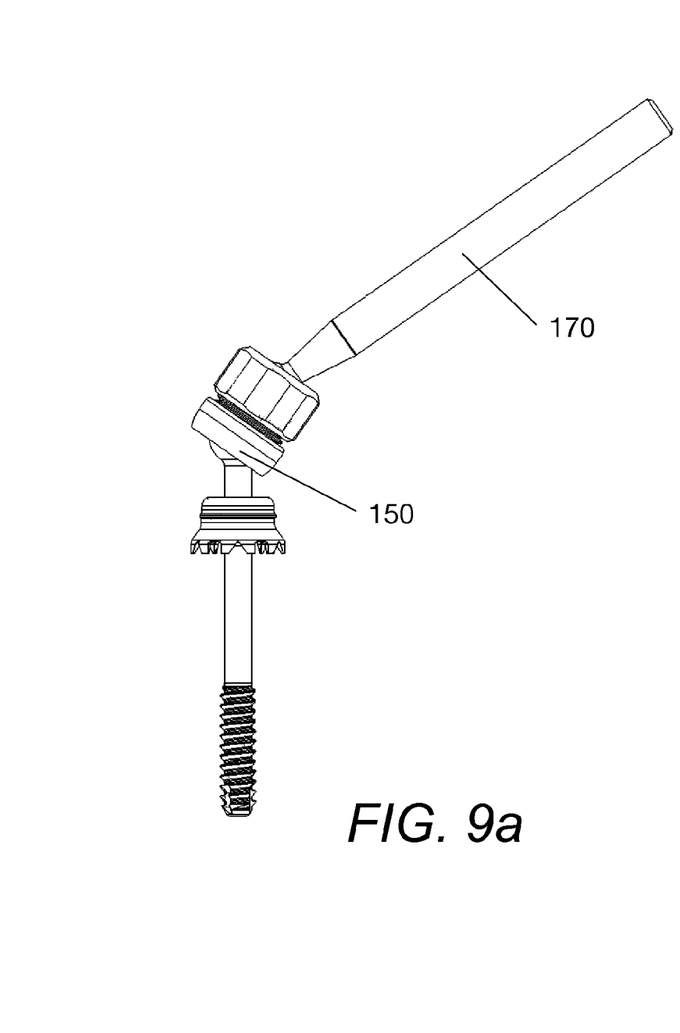
FIG. 9A is a side view of the spine fixation device of FIG. 8 with the tulip-shaped seat and the stabilization rod at an angle relative to the bone-anchoring member.
Figure 9B:
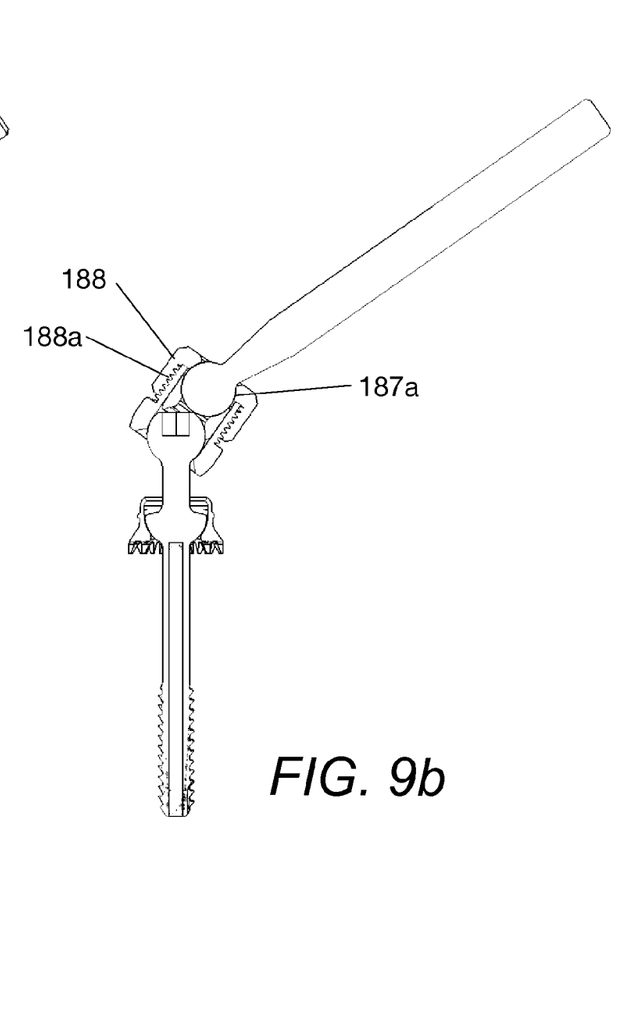
FIG. 9B is a cross-sectional view of the spine fixation device of FIG. 9A.
Figure 10:
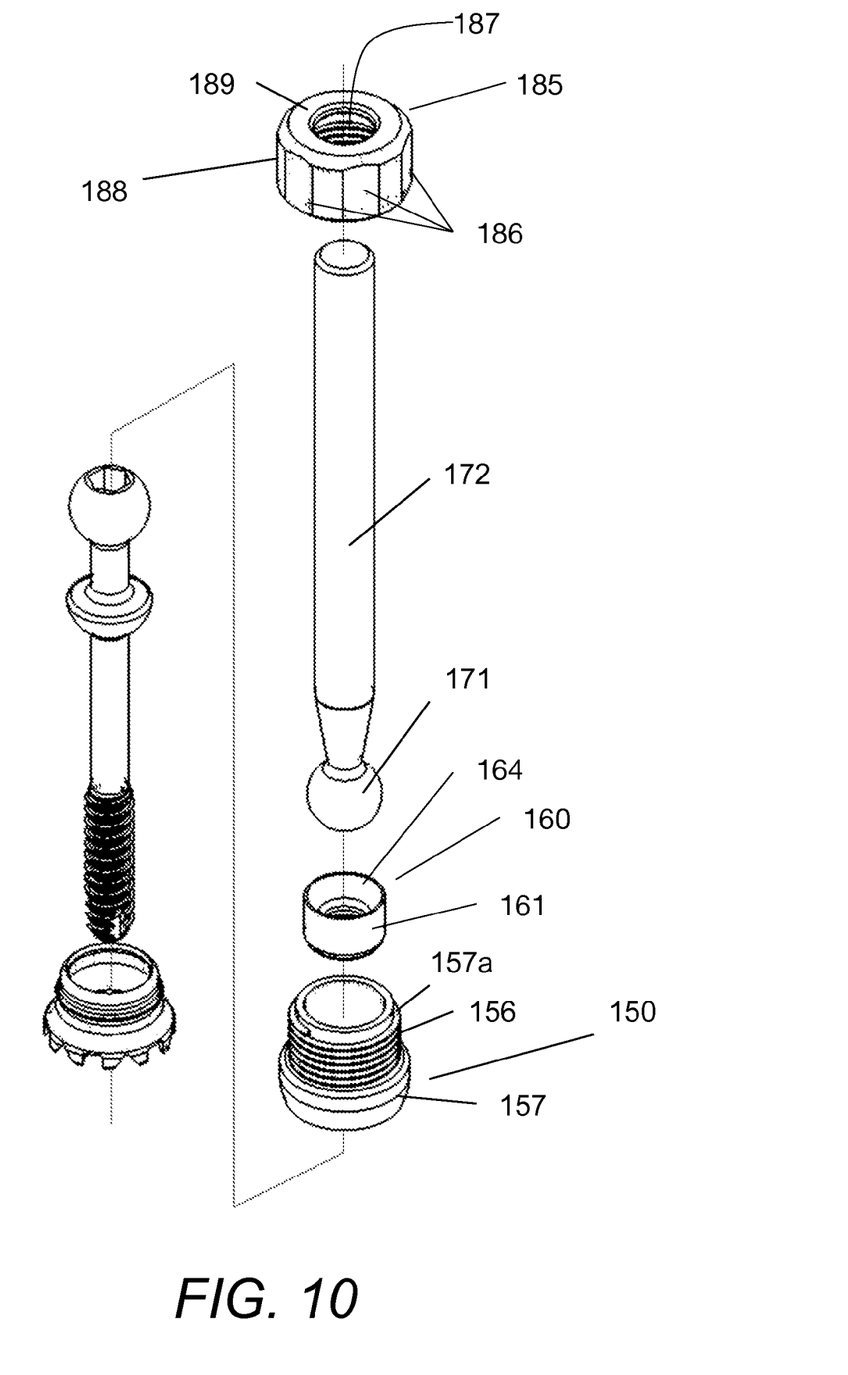
FIG. 10 is an exploded view of the spine fixation device of FIG. 8.

Referring to FIG. 8-FIG. 10, in a third embodiment 102, the seat 150 is designed and dimensioned to receive a stabilization rod 170 from the top along the axial direction 179. The seat 150 is comprised of a cylinder 157 having outer threads 156 formed on its outer surface 157a. The stabilization rod 170 includes an elongated shaft 172 terminating in a spherical head 171 at one end. In this embodiment, the rod seat 160 comprises a spherical inner wall 164 designed and dimensioned to receive the spherical head 171 of the stabilization rod 170. This embodiment also includes an outer cap 185, which includes a cylinder with a top surface 189, and a side wall 188 protruding downward from the top surface 189. The side wall 189 includes multitude of flat sides 186 arranged concentrically and equidistantly around the cylinder. Cap 185 also includes a through-opening 187 along the center axis and a curved cut 187a along the top of the through-opening 187 designed and dimensioned to capture the spherical head 171 of the stabilization rod 170. Side walls 188 include inner threads 188a designed and dimensioned to capture and engage the outer threads 156 of the seat 150.

In operation, the spherical head 171 of the stabilization rod 170 is inserted onto the rod seat 160 inside the seat 150. The stabilization rod 170 is then arranged at the desired position and angular orientation, as shown in FIG. 9a and then the outer cap 185 is driven and tightened onto the seat 150, thereby locking the stabilization rod 170 at the desired angle, the rod seat 160, the seat 150, and bone-anchoring member 110.

Figure 11:
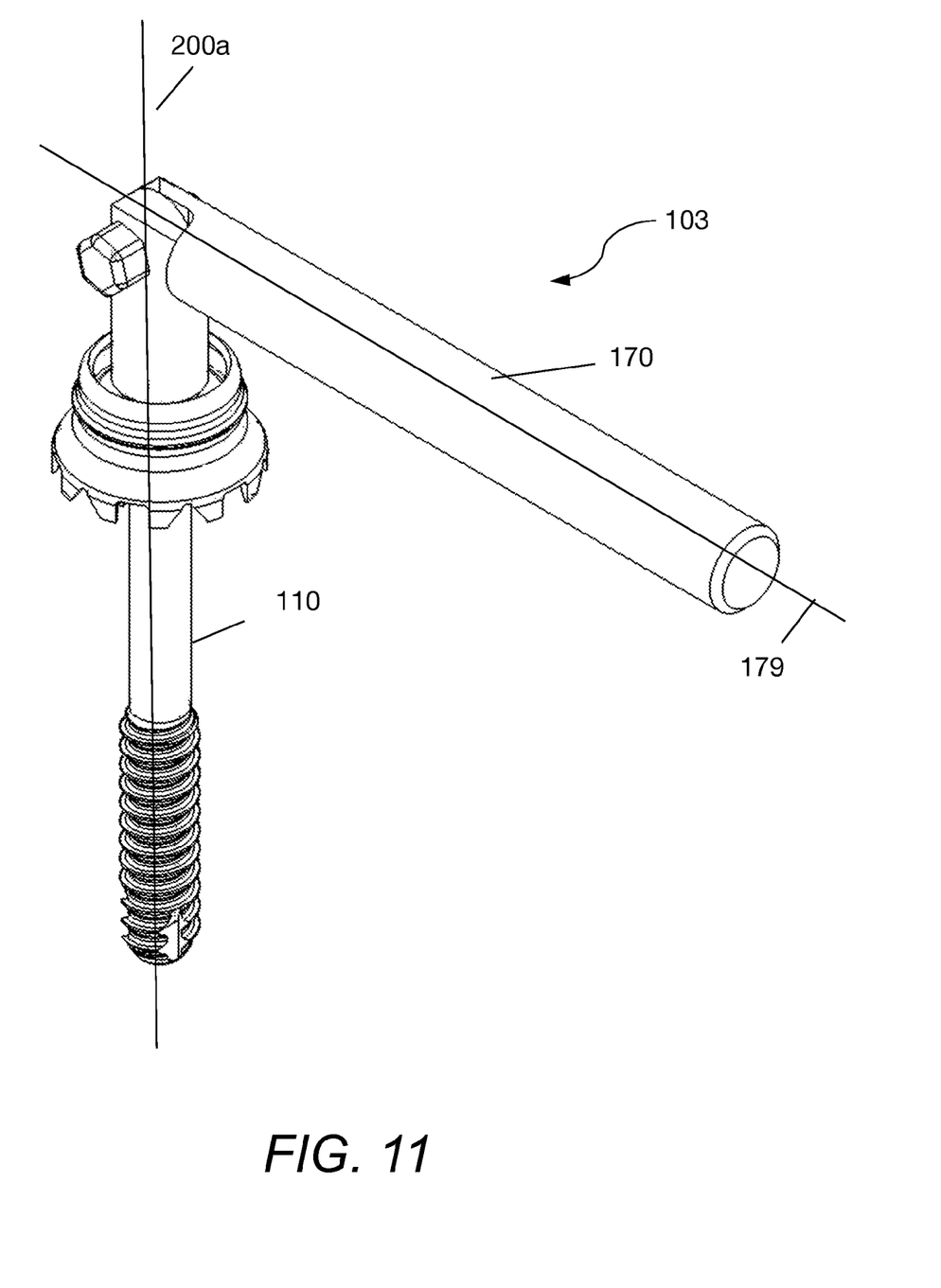
FIG. 11 is a perspective view of a fourth embodiment of the spine fixation device.
Figure 12:
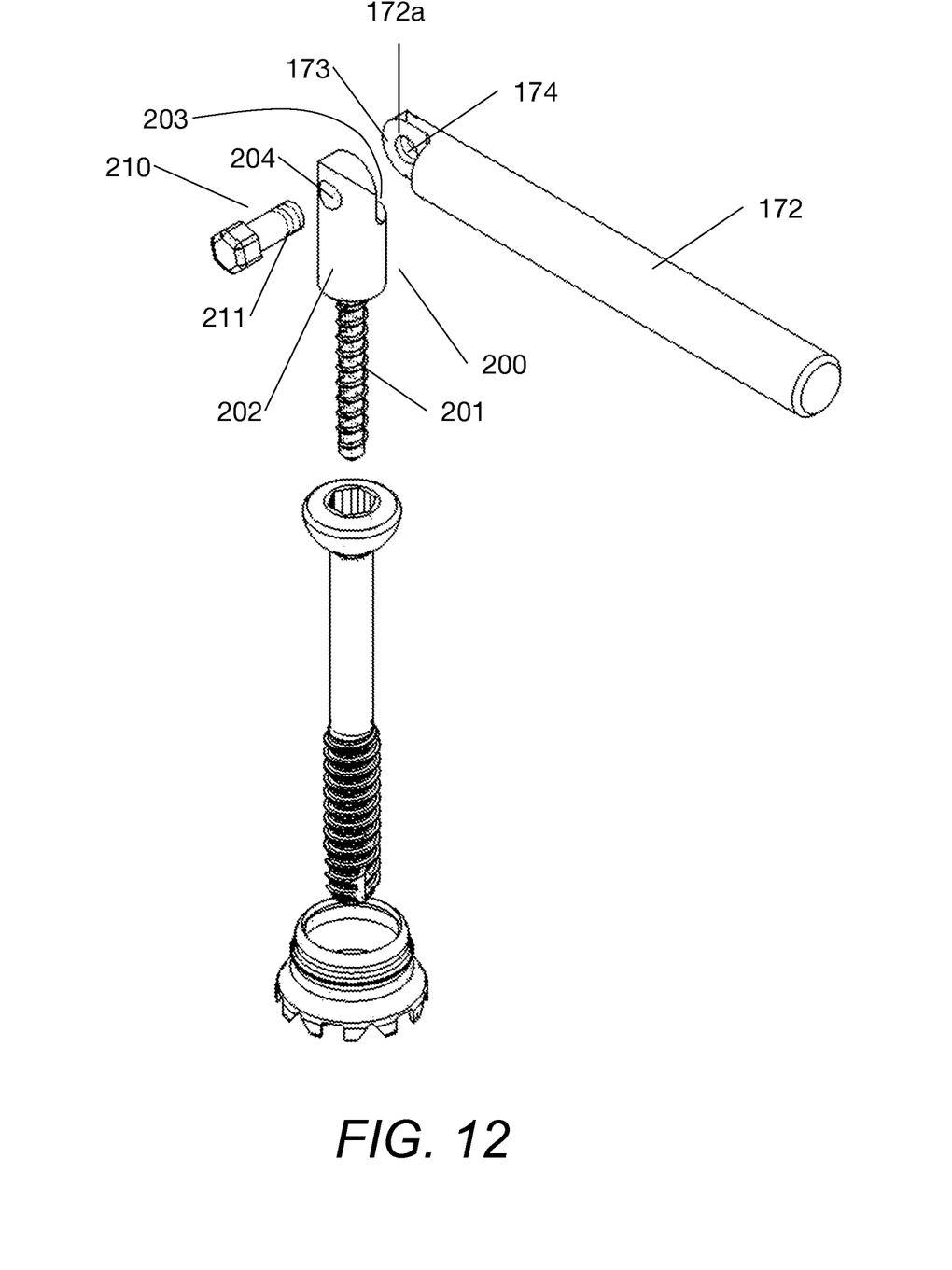
FIG. 12 is an exploded view of the spine fixation device of FIG. 11.
Figure 13:
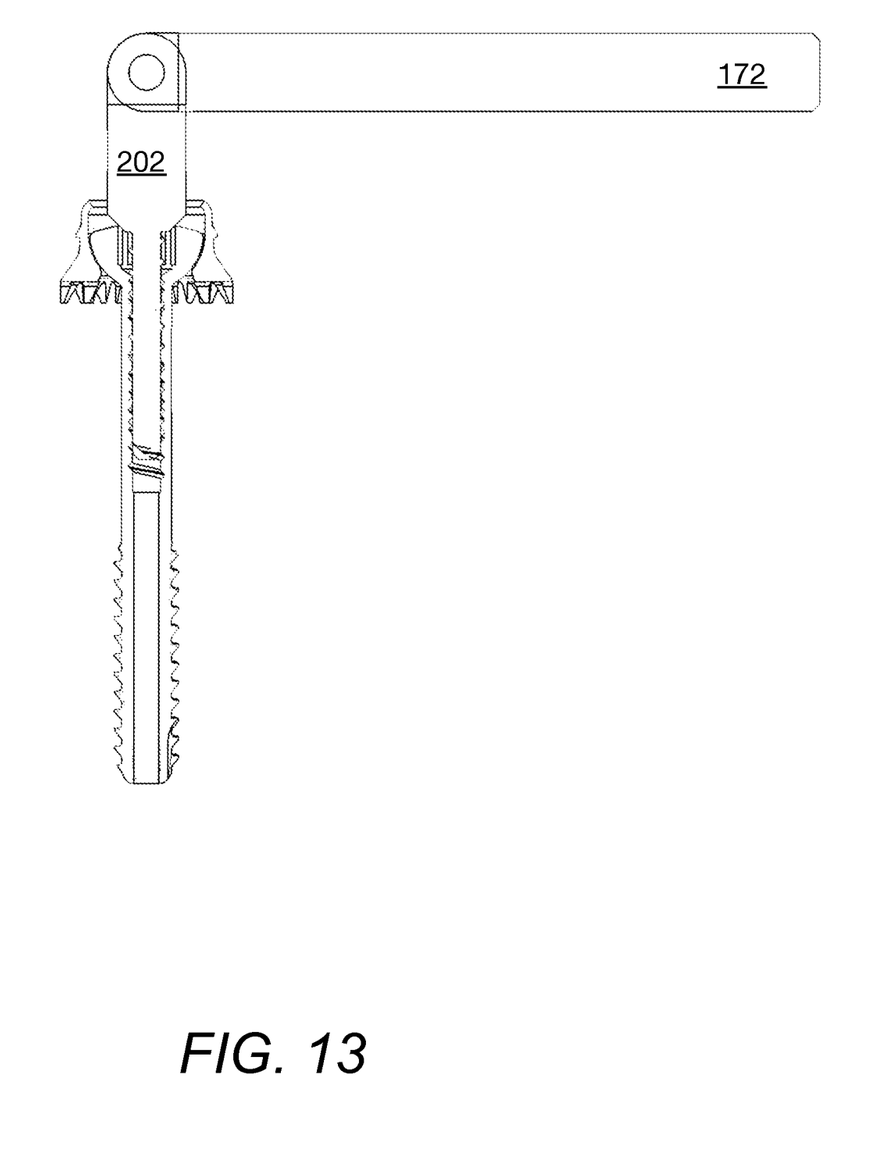
FIG. 13 is a cross-sectional side view of the spine fixation device of FIG. 11

In a fourth embodiment, the stabilization rod 170 is also inserted along the axial direction 179 and has the ability to pivot. Referring to FIG. 11-FIG. 13, in a fourth embodiment 103, the stabilization rod 170 includes an elongated shaft 172 and an end 172a having a slot cut 173 extending from a mid-plane to the outer side edge. End 172a also includes a through-opening 174 extending perpendicular to the rod axis 179 from the same side as the slot cut 173. Opening 174 includes inner threads 175 on the inner walls of the opening. In this embodiment the upper post portion comprises a pivot shaft 200. The pivot shaft 200 includes a threaded shaft 201 and a pivot post 202. Threaded shaft 201 is designed and dimensioned to be inserted into the cylindrical through-opening 122 of the bone-anchoring member 110 and to engage the inner threads 124 of the cylindrical through-opening 122. Pivot post 202 has a larger diameter than the threaded shaft 201 and has an end 202b attached to the threaded shaft 201 and an opposite end 202a. Pivot post 202 also includes a slot cut 203 formed on end 202a and extending from the top of the pivot post 202 partially downward and from the mid-plane outward to the side ends. End 202a also includes a through-opening 204 extending perpendicular to the pivot post shaft axis 200a from the slot cut 203. This embodiment also includes a pivot screw 210 designed and dimensioned to pass through the pivot post through-opening 204 and to be threaded into the through-opening 174 on the stabilization rod 170. Pivot screw 210 includes threads 211 dimensioned to capture and engage the inner threads 175 of opening 174.

In operation, the stabilization rod 170 is loosely attached to the pivot shaft 200 via the pivot screw 210. Once the bone-anchoring member 210 is in place, the threaded shaft 201 of the pivot shaft 200 is threaded into the cylindrical through-opening 122 of the bone-anchoring member 110. The stabilization rod 170 is then pivoted into the desired location and rotated at a desired angle and then the pivot screw 210 is tightened to secure the stabilization rod 170 in place.

Other embodiments are within the scope of the following claims. The screw assembly is made of metal, plastic, ceramic, bone, polymers, composites, absorbable material, biodegradable material, or combinations thereof.

Several embodiments of the present invention have been described. Nevertheless, it will be understood that various modifications may be made without departing from the spirit and scope of the invention. Accordingly, other embodiments are within the scope of the following claims.

What is claimed is:

1. A spinal screw assembly comprising:
a bone-anchoring member comprising a main shaft, a washer head and a spherical head, wherein said spherical head extends upward from the top end of the main shaft and said washer head extends laterally from a location of the main shaft between the main shaft's top end and bottom end;
a washer polyaxially rotatable and positionable around the washer head and configured to be placed at a first angle relative to the main shaft; and
a seat polyaxially rotatable and positionable around the spherical head independent from said washer and configured to be placed at a second angle relative to the main shaft, wherein said second angle is independent from said first angle.

2. The spinal screw assembly of claim 1 wherein said seat comprises a tulip-shaped body having a semispherical inner bottom portion and a cylindrical side portion extending upward from said bottom portion and wherein said bottom portion is configured to hold said spherical head and comprises a diameter equal or larger than the diameter of the spherical head, and wherein said bottom portion further comprises a through-opening dimensioned to receive and allow said main shaft to pass through and to prevent the spherical head from passing therethrough, while allowing said tulip shaped seat to polyaxially rotate and be polyaxially positioned around said spherical head.

3. The spinal screw assembly of claim 1, further comprising a stabilization rod placed perpendicular to the main shaft and wherein said cylindrical side portion of said seat comprises a horizontal channel dimensioned to receive said stabilization rod.

4. The spinal screw assembly of claim 3 further comprising a rod seat and wherein said rod seat comprises a diameter equal or smaller than the diameter of the cylindrical side portion and is configured to be placed within the cylindrical side portion and wherein said rod seat comprises a channel configured to hold said stabilization rod.

5. The spinal screw assembly of claim 4 further comprising a cap, wherein said cap comprises a ring-shaped body having outer threads in the outer surface of the ring-shaped body and inner threads in the inner surface of the ring-shaped body, and wherein said cap is configured to be placed on top of said stabilization rod and wherein said outer threads are dimensioned to engage inner threads formed in the upper inner portion of the cylindrical side portion of the seat.

6. The spinal screw assembly of claim 5 further comprising a rod-locking element comprising outer threads configured to engage the inner threads of the cap and thereby to lock said stabilization rod within said seat.

7. The spinal screw assembly of claim 1 wherein said washer head comprises a flat top and a semispherical bottom.

8. The spinal screw assembly of claim 7 wherein said washer comprises a cylindrical top portion and an outward extending bottom portion and protrusions extending downward from said bottom portion.

9. The spinal screw assembly of claim 8 wherein said washer comprises a semispherical through-opening extending from the top portion to the bottom portion and being dimensioned to receive said washer head and to prevent the washer head from passing therethrough while allowing the washer to polyaxially rotate and be polyaxially positioned around the washer head.

10. The spinal screw assembly of claim 1 wherein said main shaft further comprises bone engaging outer threads located near its bottom end.

11. The spinal screw assembly of claim 1 wherein said spherical head comprises a hexagonal top opening and wherein said hexagonal top opening extends into a cylindrical opening of the main shaft and wherein said cylindrical opening extends from the main shaft's top end to its bottom end.

12. The spinal screw assembly of claim 1 wherein said main shaft comprises adjustable length.

13. The spinal screw assembly of claim 1 wherein said main shaft comprises an upper portion and a lower portion and wherein said upper portion comprises said spherical head extending from its top end and said lower portion comprises said washer head and wherein said upper portion comprises an adjustable length and thereby said spherical head is positionable at an adjustable distance from said washer head.

14. The spinal screw assembly of claim 13 wherein said upper portion of the main shaft further comprises a threaded bottom end and wherein said washer head comprises a threaded inner opening dimensioned to receive and engage said threaded bottom end of said upper portion and wherein threading said threaded bottom end of said upper portion in or out of said threaded inner opening of said washer head adjusts the distance between the spherical head and the washer head.

15. The spinal screw assembly of claim 1 wherein said seat comprises a cylindrical body having outer threads on its outer surface and having a semispherical inner bottom portion and wherein said bottom portion is configured to hold said spherical head and comprises a diameter equal or larger than the diameter of the spherical head.

16. The spinal screw assembly of claim 15 further comprising a stabilization rod placed in line with the main shaft and having a spherical end and wherein said spherical end is configured to be placed within said cylindrical body and on top of said spherical head.

17. The spinal screw assembly of claim 16 wherein said stabilization rod comprises first and second rod components pivotally connected to each other.

18. The spinal screw assembly of claim 15 further comprising an outer cylindrical cap comprising inner threads and wherein said inner threads are dimensioned to engage the outer threads of the seat's cylindrical body.

19. The spinal screw assembly of claim 15 further comprising a rod seat dimensioned to be placed within the seat's cylindrical body and wherein said rod seat comprises a cylindrical ring having a spherical inner wall dimensioned to receive the spherical head.

20. A method for polyaxially positioning a washer and a seat relative to a main shaft of a spinal screw assembly independent from each other comprising:
providing a bone-anchoring member comprising a main shaft, a washer head and a spherical head, wherein said spherical head extends upward from the top end of the main shaft and said washer head extends laterally from a location of the main shaft between the main shaft's top end and bottom end;
providing a washer polyaxially rotatable and positionable around the washer head and placing said washer at a first angle relative to the main shaft; and
providing a seat polyaxially rotatable and positionable around the spherical head independent from said washer and placing said seat at a second angle relative to the main shaft, wherein said second angle is independent from said first angle.

* * * * *